United States Patent [19]

Horn

[11] Patent Number: 5,008,205

[45] Date of Patent: Apr. 16, 1991

[54] METHOD OF FACILITATING DETECTION OF AMINO ACID DERIVATIVES WITH ENHANCED SENSITIVITY

[75] Inventor: Marcus J. Horn, Arlington, Mass.

[73] Assignee: Hewlett-Packard Company, Palo Alto, Calif.

[21] Appl. No.: 230,580

[22] Filed: Aug. 10, 1988

[51] Int. Cl.$^5$ ............................................. G01N 33/68
[52] U.S. Cl. ........................................ 436/89; 436/92; 436/174; 530/345; 530/402
[58] Field of Search ................. 436/89, 92, 174, 161, 436/164, 172, 57, 149, 150; 530/345, 402

[56] References Cited

U.S. PATENT DOCUMENTS 4,863,870  9/1989  Stolowitz et al. ................... 436/89
4,865,994  9/1989  Tsugita et al. ...................... 436/92

Primary Examiner—Robert J. Hill, Jr.

[57] ABSTRACT

A method of detecting and identifying amino acid derivatives produced by sequential cleavage of N-terminal residues from a polypeptide chain. The polypeptide is first reacted with an isothiocyanate to produce an N-terminal-thiocarbamyl polypeptide. This derivative is then cleaved to form a cyclic ATZ derivative, which is subsequently combined with a detectable alcohol in anhydrous acid to primarily produce a stable thiocarbamyl amino acid ester. This compound may be readily detected and identified.

14 Claims, 1 Drawing Sheet

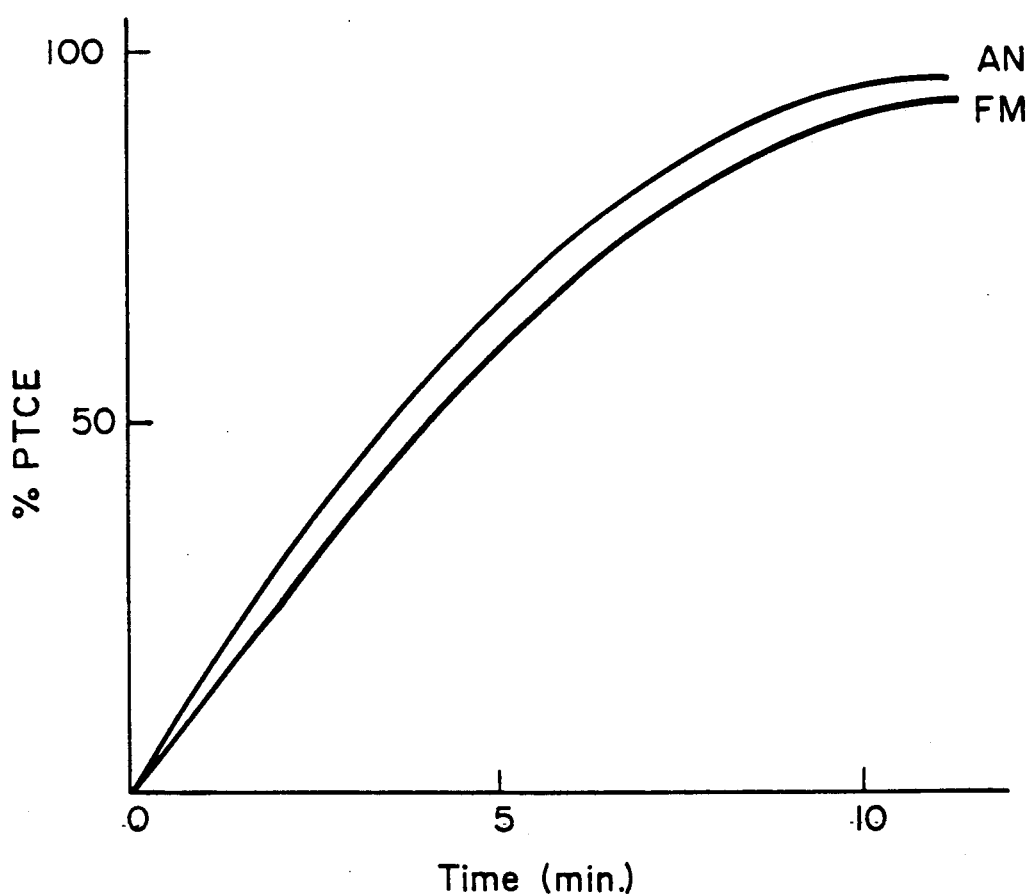

METHOD OF FACILITATING DETECTION OF AMINO ACID DERIVATIVES WITH ENHANCED SENSITIVITY

I. BACKGROUND OF THE INVENTION

A. Field of the Invention

This invention relates to a method for sequential analysis of polypeptides and proteins, and, more specifically, a method for enhancing the detectability of amino acid derivatives after chemical cleavage in order to facilitate identification.

B. Prior Art

Recent advances in medical and pharmaceutical technology have uncovered a wide range of therapeutic uses for short- and long-chain polypeptide molecules. These substances, which are composed of a chain of linked amino acid molecules control or participate in virtually all phases of cellular activity and structure. Direct control over specific metabolic levels or molecular characteristics of physiologically active polypeptides has been employed to achieve highly localized treatment of a variety of disorders, as well as promotion of desirable traits in commercial livestock. However, despite the significant potential for beneficial use of biologically active polypeptides, their size and structural complexity greatly limit the ability of scientists to understand and predict behavior in living systems.

A basic starting point for analysis of any linear chain polypeptide is determination of the precise sequence of its individual amino acid units. Researchers currently employ a variety of sequencing methodologies, the most common being the Edman degradation. In this method, successive amino acids are removed from the end of the chain by reacting the N-terminal amino acid residue with a reagent which allows selective removal of that residue. The resulting amino acid derivative is converted into a stable compound which can be chemically removed from the reaction mixture and identified.

More specifically, the Edman procedure involves initial combination of the polypeptide with phenylisothiocyanate (PITC) in basic media. The PITC couples with the free alpha-amino group of the N-terminal amino acid to form a phenylthiocarbamyl (PTC) derivative. The PTC-amino acid is then freed from the remainder of the polypeptide by cleavage of the peptide bond nearest to the PTC substituent; this requires a strongly acid reaction medium. The product of cleavage is a cyclic 2-anilino-5-thiazolinone (ATZ) derivative and a polypeptide with one amino acid less than the original. The shortened peptide has a free alpha-amino group, and may therefore be subjected to another cycle of degradation.

Because the cleaved ATZ is a derivative of the N-terminal amino acid, it could theoretically be employed for identification. This is not possible in practice, however, because of its inherent instability. Instead, the ATZ is first hydrolyzed into the PTC-amino acid, and in the same step converted into the stable 3-phenyl-2-thiohydantoin (PTH); both reactions require aqueous or alcoholic acid medium.

The PTH derivative, which incorporates the side chain of the cleaved amino acid and may therefore be used to identify that amino acid, is then removed from the reaction mixture and subjected to an identification process. This process must be highly sensitive, because most scientifically valuable polypeptides are obtainable only in very minute quantities and at significant expense. The most widely used detection techniques involve passing the PTH through a microbore high pressure liquid chromatography (HPLC) column; its rate of elution through the column will identify the amino acid from which the PTH was derived. Current equipment has produced accurate sequences with as little as 50 picomoles of sample.

All PTH-amino acid compounds show a strong absorption in the ultraviolet with a maximum at approximately 269 nm and extending to approximately 254 nm. This absorption may be utilized to detect the presence and movement of the PTH through the chromatography column. Efforts to enhance sensitivity have focused both on characteristics of the column and of the Edman reagents; the present invention relates to the latter research. Methods now practiced in the art include the use of modified forms of the initial Edman reagent, PITC, including radiolabeled PITC [Niall et al., 71 Proc. Nat. Acad. Sci. USA 384 (1974)], chromophoric isothiocyanate analogs such as phenylazophenyl isothiocyanate [Horn & Bonner, in Solid Phase Methods in Protein Sequence Analysis 163 (1977)] and dimethylaminoazobenzene isothiocyanate [Chang, Knecht Braun, in Methods in Protein Sequence Analysis 113 (1982)], fluorophoric Edman reagents [Hirano Wittmann-Liebold, Abst. JASPEC 1987, at 128], and compounds having "cryptic functionality" which are capable of undergoing subsequent reaction with chromophores or fluorophores [L'Italien & Kent, 283 J. Chromatogr. 149 (1982)].

These approaches suffer from a key limitation: although structural modification of PITC may enhance detectability of the resulting PTH compound on a molecular basis, the presence of by-products from the Edman degradation (e.g. phenylthiourea and diphenylthiourea derivatives) that absorb at similar wavelengths will reduce overall spectroscopic detectability of the PTH in solution. Hence, attempts to achieve significant increases in detection capability must focus both on the system's signal-to-noise ratio as well as sensitivity to the amino acid derivative in isolation.

An additional disadvantage of these methods is reduced reagent reactivity frequently encountered as a consequence of the detection-enhancing structural modification. Like an unimproved signal-to-noise ratio, lower reactivity will sacrifice a proportionate amount of the gains achieved by the enhancement.

An alternative strategy is to convert one of the intermediate Edman compounds into a more easily detected derivative. Tsugita et al. [103 J. Biochem. 399 (1988)] have recently adopted this approach by exposing the ATZ-amino acid to a radiolabeled primary amine to yield a sensitized PTC derivative. This procedure, while enhancing sensitivity, also suffers from several disadvantages. Although the radiolabeled amine compounds are stable when purchased as the HCl salt, basic conditions are required to remove salts so that the attachment reaction may proceed. Furthermore, the presence of any trace of aqueous acid will induce conversion of the labeled PTC into a PTH derivative; this conversion will remove the label. Because the Edman cleavage reaction requires an acidic environment, use of Tsugita's method requires complete removal of the acid cleavage reagent prior to introduction of the labeled compound. In addition, any acid contamination of the labeled PTC derivative while in storage will destroy the enhanced detectability.

II. DESCRIPTION OF THE INVENTION

A. Brief Summary of the Invention

We have found a method of efficiently converting the ATZ Edman intermediate into a modified, readily detectable PTC derivative under very convenient reactive conditions. Combining a desired alcohol, which contains a functional group or label that enhances its detectability, with the ATZ-amino acid Edman intermediate in an acid environment results in formation of the PTC amino acid ester. Under the standard Edman procedure, this compound would undergo equilibrated conversion into the PTH derivative in a reaction that cleaves the detection label. However, we have found that it is possible to shift the equilibrium strongly in the direction of the PTC amino acid ester (which contains the label) through judicious choice of the alcohol and maintenance of anhydrous conditions. The labeled PTC amino acid ester may be observed in extremely minute amounts through use of a detection technique suitable to the particular label chosen. Resolution of the PTC amino acid esters (and consequent identification of the isolated amino acid) may be effected by means of well-known techniques of reverse phase HPLC, with typical sensitivity increases of 10–100 times that of current methods. The invention is amenable to spectroscopic, fluorescence, radiolabeling and electrochemical chromatographic detection methods.

This method is highly favored both in terms of laboratory convenience, percent yield and detectability of the final product. Since the reaction environment required for production and maintenance of the PTC amino acid ester is identical to that necessary to perform the prior Edman step, no stringent acid removal step is required. Steric hindrance associated with the sensitivity-enhancing moieties actually promotes the desired reaction by disfavoring the cyclic PTH conformation. Where spectroscopic means of detection are employed, the sensitivity achieved with the present invention retains a very high signal-to-noise ratio, since the product's absorbance characteristics differ significantly from Edman by-products; this is in marked contrast to Edman modifications that result in a PTH end product.

B. Objects of the Invention

Accordingly, it is an object of the invention to provide a method of producing a high-yield, readily detectable amino acid derivative in connection with use of the Edman procedure of sequential polypeptide degradation without sacrificing overall reactivity or laboratory convenience.

It is a further object of the invention to provide a method of producing such an amino acid derivative whereby detection of the derivative will not be impeded by the presence of Edman by-products with similar absorbance characteristics.

It is yet a further object of the invention to provide a method of producing amino acid derivatives that are detectable by a variety of laboratory techniques.

C. Detailed Description of the Invention

The foregoing and other and further objects of the invention will be understood more readily from the following detailed description of the invention, when taken in conjunction with the single Figure of the drawing, which shows a plot of the percent yield of PTC amino acid ester (PTCE) obtained utilizing the reaction procedures described in the Example.

In a preferred embodiment, fluorenemethyl alcohol or 9-anthracenemethanol are reacted with an ATZ-amino acid derivative obtained using the Edman procedure in a reaction mixture of anhydrous HCl and benzene.

Further embodiments of the invention and their properties will be evident from the following example, given by way of illustration:

EXAMPLE

Conversion of ATZ-norleucine to PTC-norleucine esters

ATZ-norleucine and anhydrous trifluoroacetic acid (products of the Edman cleavage step) were delivered into a conical-bottomed reaction vessel through a Teflon transport tube. At mild heating (35–40° C.), gaseous nitrogen was bubbled into the mixture to evaporate the trifluoroacetic acid. Anhydrous HCl (1.0 N) in benzene and 10 equivalents of fluorenemethyl alcohol (FM) or 9-anthracenemethanol (AN) were then introduced, and the mixture heated at 60° C. for 10–12 minutes. With the reaction complete, the mixture was dried down to eliminate acid. A mixture of methanol and dichloroethane was then used to extract the product into a fraction collector, where it was stored for analysis. As may be seen in FIG. 1, the yield of the PTC amino acid ester is nearly 100%.

III. CONCLUSION

From the foregoing, it will be seen that we have provided an improved method of enhancing detectability of amino acid moieties that have been separated utilizing the Edman degradation procedure. The method is simple, convenient to use, highly efficient and flexible.

It will be understood by those skilled in the art that various changes may be made in the foregoing without departing from either the spirit or scope of the invention. For example, although highly colored or highly fluorescent alcohols have been employed in the embodiments of the invention disclosed herein, different moieties may be attached to readily available alcohols to facilitate different techniques of detection, such as electrochemical, fluorescent or radiolabeling methods. As an additional example, evaporation of the acid cleavage reagent prior to esterification would not be necessary if a non-carboxylic acid such as originally used by Edman were employed.

I claim:

1. A method of enhancing the detectability of an amino acid in order to facilitate identification, comprising the steps of converting the amino acid to a 5-thiazolinone amino acid derivative and reacting the derivative with a mixture of an anhydrous acid and an alcohol to primarily produce a thiocarbamyl amino acid ester.

2. The method of claim 1 in which said acid comprises hydrochloric acid.

3. The method of claim 1 in which said alcohol comprises fluorenemethyl alcohol.

4. The method of claim 1 in which said alcohol comprises ]-anthracenemethanol.

5. The method of claim 1 wherein the amino acid derivative is obtained using a sequential chemical degradative procedure.

6. The method of claim 5 wherein the degradative procedure utilizes an isothiocyanate compound.

7. The method of claim 6 wherein the isothiocyanate compound is phenylisothiocyanate.

8. The method of claim 1 wherein the alcohol is colored.

9. The method of claim 1 wherein the alcohol is fluorescent.

10. The method of claim 1 wherein the alcohol is electrochemically active.

11. The method of claim 1 wherein the alcohol is radiolabeled.

12. A method of determining the identity of the N-terminal amino acid of a polypeptide, comprising the steps of:
 a. reacting the polypeptide with PITC to form an N-terminal-PTC derivative of the polypeptide;
 b. cleaving the N-terminal-PTC amino acid from the remainder of the polypeptide to form a cyclic ATZ derivative;
 c. reacting the cyclic ATZ derivative with a detectable alcohol in anhydrous acid to primarily produce a PTC amino acid ester;
 d. detecting and identifying the PTC amino acid ester.

13. The method of claim 12 wherein the PTC amino acid ester is primarily produced by using a sterically hindered alcohol.

14. The method of claim 12 wherein the PTC amino acid ester is primarily produced by using an alcohol that, when combined with the cyclic ATZ, disfavors rearrangement to the cyclic conformation of PTH.

* * * * *